(12) United States Patent
Stamp et al.

(10) Patent No.: US 8,747,357 B2
(45) Date of Patent: Jun. 10, 2014

(54) AUTOINJECTOR

(75) Inventors: Kevin Stamp, Chapeltown (GB); Ian Charles Cleathero, Melton Mowbray (GB)

(73) Assignee: The Medical House Limited, Hertfordshire (GB)

( * ) Notice: Subject to any disclaimer, the term of this patent is extended or adjusted under 35 U.S.C. 154(b) by 1287 days.

(21) Appl. No.: 12/601,220

(22) PCT Filed: Dec. 18, 2007

(86) PCT No.: PCT/GB2007/004870
§ 371 (c)(1),
(2), (4) Date: May 27, 2011

(87) PCT Pub. No.: WO2008/075033
PCT Pub. Date: Jun. 26, 2008

(65) Prior Publication Data
US 2011/0282278 A1    Nov. 17, 2011

(30) Foreign Application Priority Data

Dec. 18, 2006  (GB) .................................. 0625169.8

(51) Int. Cl.
*A61M 5/20* (2006.01)
*A61M 5/315* (2006.01)

(52) U.S. Cl.
USPC .......................................... 604/134; 604/218

(58) Field of Classification Search
USPC ......... 604/110, 218, 220, 155, 131, 136, 137, 604/117, 134, 70, 506
See application file for complete search history.

(56) References Cited

U.S. PATENT DOCUMENTS

| 60,917 A | 1/1867 | Brown |
|---|---|---|
| 3,702,608 A | 11/1972 | Tibbs |
| 3,756,242 A | 9/1973 | Coss |
| 3,797,489 A | 3/1974 | Sarnoff |
| 3,811,442 A | 5/1974 | Maroth |
| 4,617,016 A | 10/1986 | Blomberg |

(Continued)

FOREIGN PATENT DOCUMENTS

| DE | 102004060146 A1 | 8/2005 |
|---|---|---|
| EP | 0453212 | 10/1991 |

(Continued)

OTHER PUBLICATIONS

Official Action for U.S. Appl. No. 12/161,776, mailed Oct. 6, 2010, 21 pages.

(Continued)

*Primary Examiner* — Nicholas Lucchesi
*Assistant Examiner* — Brooke Matney
(74) *Attorney, Agent, or Firm* — Sheridan Ross P.C.

(57) ABSTRACT

An autoinjector comprising an outer housing in which can be mounted a syringe for holding a volume of medicament, the syringe for holding medicament having a needle at one end thereof, a syringe holder for supporting the syringe in an axial position relative to the outer housing, and an intermediate housing at least part of which is located within said outer housing, characterised in that said intermediate housing is provided with a blocking means capable of abutting the syringe or the syringe holder so as to be capable of preventing forward axial movement of the syringe when a forward axial force is applied to said needle before actuation of the autoinjector to deliver an injection, but incapable of preventing forward axial movement of the syringe during actuation of the autoinjector to deliver an injection.

18 Claims, 6 Drawing Sheets

(56) References Cited

U.S. PATENT DOCUMENTS

| | | | |
|---|---|---|---|
| 4,913,699 A | 4/1990 | Parsons | |
| 4,923,447 A | 5/1990 | Morgan | |
| 4,958,622 A | 9/1990 | Selenke | |
| 4,976,724 A | 12/1990 | Nieto et al. | |
| 5,000,744 A | 3/1991 | Hoffman et al. | |
| 5,024,656 A | 6/1991 | Gasaway et al. | |
| 5,042,977 A | 8/1991 | Bechtold et al. | |
| 5,078,698 A | 1/1992 | Stiehl et al. | |
| 5,167,632 A | 12/1992 | Eid et al. | |
| 5,211,625 A | 5/1993 | Sakurai et al. | |
| 5,300,030 A | 4/1994 | Crossman et al. | |
| 5,320,609 A | 6/1994 | Haber et al. | |
| 5,478,316 A | 12/1995 | Bitdinger et al. | |
| 5,568,261 A | 10/1996 | Wakai et al. | |
| 5,599,309 A | 2/1997 | Marshall et al. | |
| 5,634,906 A | 6/1997 | Haber et al. | |
| 5,658,261 A | 8/1997 | Neer et al. | |
| 5,681,291 A | 10/1997 | Galli | |
| 5,779,675 A | 7/1998 | Reilly et al. | |
| 5,779,677 A | 7/1998 | Frezza | |
| 6,203,530 B1 | 3/2001 | Stewart, Sr. | |
| 6,210,369 B1 | 4/2001 | Wilmot et al. | |
| 6,264,629 B1 | 7/2001 | Landau | |
| 6,270,479 B1 | 8/2001 | Bergens et al. | |
| 6,280,421 B1 | 8/2001 | Kirchhofer et al. | |
| 6,544,234 B1 | 4/2003 | Gabriel | |
| 6,605,072 B2 | 8/2003 | Struys et al. | |
| 6,607,510 B2 | 8/2003 | Landau | |
| 6,620,137 B2 | 9/2003 | Kirchhofer et al. | |
| 6,632,198 B2 | 10/2003 | Caizza | |
| 6,656,163 B1 | 12/2003 | Marshall et al. | |
| 6,689,093 B2 | 2/2004 | Landau | |
| 6,752,781 B2 | 6/2004 | Landau et al. | |
| 6,981,499 B2 | 1/2006 | Anderson et al. | |
| 7,118,552 B2 | 10/2006 | Shaw et al. | |
| 7,156,823 B2 | 1/2007 | Landau et al. | |
| 7,635,356 B2 | 12/2009 | Stamp | |
| 7,645,265 B2 | 1/2010 | Stamp | |
| 7,976,499 B2 | 7/2011 | Grunhut et al. | |
| 2001/0005781 A1 | 6/2001 | Bergens et al. | |
| 2003/0105430 A1 | 6/2003 | Lavi et al. | |
| 2003/0236502 A1 | 12/2003 | De la Serna et al. | |
| 2004/0039336 A1 | 2/2004 | Amark et al. | |
| 2005/0027255 A1 | 2/2005 | Lavi et al. | |
| 2005/0165349 A1 | 7/2005 | Stamp | |
| 2006/0100589 A1 | 5/2006 | Lin | |
| 2006/0270984 A1 | 11/2006 | Homman | |
| 2007/0017533 A1 | 1/2007 | Wyrick | |
| 2007/0173770 A1 | 7/2007 | Stamp | |
| 2007/0265568 A1 | 11/2007 | Tsals et al. | |
| 2008/0195056 A1 | 8/2008 | Bishop et al. | |
| 2009/0012471 A1 | 1/2009 | Harrison | |
| 2010/0069846 A1 | 3/2010 | Stamp | |
| 2010/0130930 A1 | 5/2010 | Stamp et al. | |
| 2010/0152655 A1 | 6/2010 | Stamp | |
| 2012/0130342 A1 | 5/2012 | Cleathero | |
| 2012/0136303 A1 | 5/2012 | Cleathero | |

FOREIGN PATENT DOCUMENTS

| | | |
|---|---|---|
| EP | 0518416 | 12/1992 |
| EP | 0740942 | 11/1996 |
| EP | 0864335 | 9/1998 |
| EP | 1323447 | 7/2003 |
| EP | 2080532 | 7/2009 |
| FR | 2899482 | 10/2007 |
| GB | 886444 | 1/1962 |
| GB | 2443606 | 9/1994 |
| GB | 2388033 A | 11/2003 |
| GB | 2396298 | 6/2004 |
| GB | 2397767 A | 8/2004 |
| GB | 2410188 | 7/2005 |
| GB | 2414398 A | 11/2005 |
| WO | WO 94/21316 | 9/1994 |
| WO | WO 99/10030 | 3/1999 |
| WO | 9922792 A1 | 5/1999 |
| WO | WO 00/09186 | 2/2000 |
| WO | WO 01/93926 | 12/2001 |
| WO | WO 02/17996 | 3/2002 |
| WO | WO 02/47746 | 6/2002 |
| WO | WO 02/070051 | 9/2002 |
| WO | WO 03/097133 | 11/2003 |
| WO | WO 03/099358 | 12/2003 |
| WO | WO 2004/108194 | 12/2004 |
| WO | WO 2005/009515 | 2/2005 |
| WO | WO 2005/009520 | 2/2005 |
| WO | WO 2005/046765 | 5/2005 |
| WO | WO 2005/070481 A | 8/2005 |
| WO | WO 2005/097252 | 10/2005 |
| WO | 2005115507 A1 | 12/2005 |
| WO | WO 2005/115512 | 12/2005 |
| WO | WO 2006/052737 | 5/2006 |
| WO | WO 2006/106291 | 10/2006 |
| WO | WO 2006/106295 | 10/2006 |
| WO | WO 2006/111862 | 10/2006 |
| WO | WO 2007/008257 | 1/2007 |
| WO | WO 2007/036676 | 4/2007 |
| WO | WO 2007/083115 | 7/2007 |
| WO | WO 2007/132353 A | 11/2007 |
| WO | WO 2008/075033 | 6/2008 |
| WO | WO 2008/107670 | 9/2008 |
| WO | WO 2008/113864 | 9/2008 |
| WO | WO 2010/026414 | 3/2010 |

OTHER PUBLICATIONS

Official Action for U.S. Appl. No. 11/387,645, mailed Aug. 25, 2010, 16 pages.
International Search Report issued by the European Patent Office on Mar. 19, 2008 for International Application No. PCT/GB2007/004870.
Written Opinion issued by the European Patent Office on Mar. 19, 2008 for International Application No. PCT/GB2007/004870.
International Preliminary Report on Patentability issued on Jun. 24, 2009 for International Application No. PCT/GB2007/004870.
Search Report prepared by the United Kingdom Intellectual Property Office on Aug. 26, 2009, for Application No. GB0906973.3, 2 pages.
Authorized Officer Reinbold, International Search Report for International Application No. PCT/GB2010/050161, dated May 17, 2010, 5 pages.
Authorized Officer Reinbold, Written Opinion for International Application No. PCT/GB2010/050161, issued Aug. 5, 2011, 5 pages.
Authorized Officer Mulhausen, International Preliminary Report on Patentability issued on Aug. 9, 2011 for International Application No. PCT/GB2010/050161, 6 pages.
Official Action for U.S. Appl. No. 12/161,776, mailed Aug. 29, 2012, 8 pages.
Notice of Allowance for U.S. Appl. No. 13/189,286, mailed Jun. 22, 2012, 6 pages.
"Relaxed." Merriam-Webster Dictionary, found on-line at http://www.merriam-webster.com/dictionary/relaxed, Dec. 21, 2011.
Notice of Allowance for U.S. Appl. No. 12/530,107, mailed Jan. 25, 2012, 8 pages.
Official Action for U.S. Appl. No. 11/387,645, mailed Dec. 21, 2011, 21 pages.
Official Action for U.S. Appl. No. 13/189,286, mailed Jan. 4, 2012, 9 pages.
Restriction Requirement for U.S. Appl. No. 12/623,960, mailed Jan. 5, 2012, 6 pages.
Official Action for U.S. Appl. No. 12/623,960, mailed Mar. 5, 2012, 11 pages.
U.S. Appl. No. 13/140,483, filed Jun. 17, 2011, Cleathero.
U.S. Appl. No. 13/189,286, filed Jul. 22, 2011, Stamp et al.
Authorized Officer Reinbold, International Preliminary Report on Patentability for International (PCT) Patent Application No. PCT/GB2005/000223, mailed Jan. 23, 2006, 6 pages.
Authorized Officer Reinbold, Written Opinion for International (PCT) Patent Application No. PCT/GB2005/000223, mailed Jun. 22, 2005, 7 pages.

(56) References Cited

OTHER PUBLICATIONS

UK Search Report for Application No. GB0602411.1, dated Apr. 7, 2006, 4 pages.
Corrected Search Report under Section 17 for Application No. GB0620163.6, dated Nov. 24, 2006, 1 page.
International Search Report for International (PCT) Patent Application No. PCT/GB2007/000141, mailed May 5, 2007, 2 pages.
Authorized Officer Bjorklund, Written Opinon for International (PCT) Patent Application No. PCT/GB2007/000141, mailed May 5, 2007, 7 pages.
Authorized Officer Mulhausen, International Preliminary Report on Patentability for International (PCT) Patent Application No. PCT/GB2007/000141, mailed Jul. 29, 2008, 8 pages.
Authorized Officer Guidoin, International Search Report for International (PCT) Application No. PCT/GB2008/000741, mailed Dec. 23, 2008, 8 pages.
Authorized Officer Urack, Written Opinon for International (PCT) Patent Application No. PCT/GB2008/00741, mailed Dec. 23, 2008, 15 pages.
Authorized Officer Mulhausen, International Preliminary Report on Patentability for International (PCT) Application No. PCT/GB2008/000741, mailed Sep. 17, 2009, 13 pages.
UK Search Report for Application No. GB0804021.4, dated Jul. 1, 2008, 4 pages.
UK Search Report for Application No. GB0704351.6, dated Jun. 7, 2007, 4 pages.
Authorized Officer Bjorklund, International Search Report issued by the European Patent Office for International (PCT) Application No. PCT/GB2009/051716, mailed May 19, 2010, 5 pages.
Authorized Officer Mulhausen, International Preliminary Report on Patentability for International (PCT) Application No. PCT/GB2009/051716, mailed Jun. 23, 2011, 9 pages.
Official Action for U.S. Appl. No. 10/767,859, mailed Feb. 24, 2006, 8 pages.
Official Action for U.S. Appl. No. 10/767,859, mailed Sep. 12, 2006, 10 pages.
Official Action for U.S. Appl. No. 10/767,859, mailed Jun. 5, 2007, 8 pages.
Official Action for U.S. Appl. No. 10/767,859, mailed Dec. 28, 2007, 8 pages.
Official Action for U.S. Appl. No. 10/767,860, mailed Mar. 14, 2006, 8 pages.
Official Action for U.S. Appl. No. 10/767,860, mailed Aug. 22, 2006, 8 pages.
Official Action for U.S. Appl. No. 10/767,860, mailed Dec. 15, 2006, 3 pages.
Official Action for U.S. Appl. No. 10/767,860, mailed Apr. 10, 2007, 7 pages.
Official Action for U.S. Appl. No. 10/767,860, mailed Sep. 24, 2007, 9 pages.
Official Action for U.S. Appl. No. 10/767,860, mailed Jan. 11, 2008, 8 pages.
Official Action for U.S. Appl. No. 10/767,860, mailed Jun. 12, 2008, 6 pages.
Advisiory Action for U.S. Appl. No. 10/767,860, mailed Sep. 5, 2008, 3 pages.
Official Action for U.S. Appl. No. 10/767,860, mailed Dec. 2, 2008, 5 pages.
Interview Summary for U.S. Appl. No. 10/767,860, mailed Feb. 2, 2009, 4 pages.
Notice of Allowance for U.S. Appl. No. 10/767,860, mailed Aug. 27, 2009, 8 pages.
Restriction Requirement for U.S. Appl. No. 11/387,645, mailed May 28, 2009, 7 pages.
Official Action for U.S. Appl. No. 11/387,645, mailed Feb. 11, 2011, 29 pages.
Official Action for U.S. Appl. No. 11/387,645, mailed Jul. 14, 2011, 19 pages.
Official Action for U.S. Appl. No. 10/597,379, mailed Jul. 31, 2008, 12 pages.
Official Action for U.S. Appl. No. 10/597,379, mailed Feb. 23, 2009, 9 pages.
Notice of Allowance for U.S. Appl. No. 10/597,379, mailed Sep. 2, 2009, 11 pages.
Official Action for U.S. Appl. No. 12/161,776, mailed May 11, 2011, 11 pages.
Official Action for U.S. Appl. No. 12/530,107, mailed Apr. 14, 2011, 10 pages.
Official Action for U.S. Appl. No. 11/387,645, mailed Sep. 17, 2010, 29 pages.
Communication pursuant to Article 94(3) EPC for European Patent Application No. 07704923.7, dated Aug. 2, 2011, 7 pages.
Official Action for U.S. Appl. No. 12/530,107, mailed Aug. 4, 2011, 9 pages.
Formalities Officer Sulis, Communication pursuant to Rule 114(2) EPC for European Patent Application No. 07704923.4, mailed Sep. 29, 2010, 9 pages.
Official Action for U.S. Appl. No. 13/147,568 mailed Sep. 6, 2013, 10 pages.
Notice of Allowance for U.S. Appl. No. 12/161,776, mailed Jun. 7, 2013, 9 pages.
Official Action for U.S. Appl. No. 13/265,801, mailed Jun. 21, 2013, 8 pages.
Official Action for U.S. Appl. No. 11/387,645, mailed Nov. 12, 2013, 13 pages.
Notice of Allowance for U.S. Appl. No. 12/161,776, mailed Oct. 15, 2013, 10 pages.
Official Action for U.S. Appl. No. 13/147,568 mailed Oct. 23, 2013, 8 pages.

AUTOINJECTOR

CROSS-REFERENCE TO RELATED APPLICATIONS

This application is a national stage application under 35 U.S.C. 371 of PCT Application No. PCT/GB2007/004870 having an international filing date of 18 Dec. 2007, which designated the United States, which PCT application claimed the benefit of Great Britain Application No. 0625169.8 filed 18 Dec. 2006, the entire disclosure of each of which are hereby incorporated herein by reference.

This invention relates to the field of autoinjectors for the administration of liquid medication, for example, interferon.

BACKGROUND

An autoinjector is an automatic injection device designed to facilitate delivery of a dose of medicament to a patient through a hypodermic needle, the injection usually being administered by the patient themselves. An autoinjector works, for example, by delivering an injection automatically upon actuation by the patient pressing a button, moving a lever or part of a housing etc. This is in contrast to a conventional manual syringe where the patient themselves needs to directly depress a plunger into a barrel containing medicament in order to effect the injection. The terms "autoinjector" and "injection device" are used interchangeably in the following description.

One typical known autoinjector is described in WO00/09186 (Medi-Ject Corporation) for "Needle assisted jet injector" and this document gives a useful summary of other prior art devices.

Another autoinjector is described in our co-pending international patent application, published under number WO 2005/070481. Some of the reference numerals in the present application correspond with the equivalent components in the device described in WO 2005/070481. This device requires that the needle is moved axially so that it can appear beyond the end of the nozzle for the duration of the injection, after which the needle retracts automatically, so that it is never in sight of the user. The device also requires that the plunger is moved axially so that medicament is ejected. The overall complexity of the autoinjector is significantly reduced by both of these requirements being effected by one component, namely an inner housing and the device has the significant advantage that it can be built around a conventional or standard syringe presentation.

The injection device of WO 2005/070481 is designed to be used in conjunction with a standard drug presentation e.g. a syringe comprising a needle, barrel preloaded with medicament and a plunger. The present invention is relevant to any injection device for use in conjunction with a syringe (whether preloaded or not and whether single-use or reusable), not only the device described in WO 2005/070481.

In the known device described in our co-pending patent application no WO 2005/070481, the syringe is supported within the injection device by a barrel or syringe holder 9. The syringe holder is sometimes referred to as a "syringe support means". The syringe holder 9 comprises an elongate housing which closely surrounds the glass barrel of the syringe. An improved syringe holder is described in our co-pending UK patent application number 0620163.6 filed 12 Oct. 2006. During delivery of an injection, the syringe holder and syringe contained therein are moveable along an axial path, substantially parallel with the longitudinal axis of the autoinjector.

A potential problem arises when the needle cover of an autoinjector is removed, in preparation for delivering an injection. An autoinjector is usually supplied to the patient with the needle of the syringe embedded in a rubber or other elastomeric sheath. The rubber sheath is in turn closely surrounded by a rigid needle cover which protects the needle from damage. Both the rubber sheath and rigid needle cover need to be removed before an injection can be delivered. Actuation of the autoinjector to deliver an injection occurs by actuating the main energy source (usually a spring) of the autoinjector. Prior to that, removal of the rubber sheath and rigid needle cover is usually achieved by providing some kind of gripping means on the interior of the autoinjector's end-cap, so that when the patient pulls the end-cap off the device, the rubber sheath and rigid needle cover are simultaneously removed with the end-cap. In a device such as that described in WO 2005/070481, even when ready to deliver an injection, the unsheathed needle is not exposed to the patient because it is located wholly within the autoinjector's housing.

As the rubber sheath is pulled from the needle, the needle is subjected to a forward axial force which in turn pulls the syringe (to which the needle is attached), moving it slightly axially forward. When the needle comes free of the rubber sheath, the forward axial force is suddenly removed and the needle and syringe can "bounce back" against other internal components of the autoinjector to its original axial position.

It is therefore an object of the present invention to provide an improved autoinjector which seeks to alleviate the above-described problems.

SUMMARY OF THE INVENTION

According to a first aspect of the invention, there is provided an autoinjector comprising
  an outer housing in which can be mounted a syringe for holding a volume of medicament, the syringe for holding medicament having a needle at one end thereof,
  a syringe holder for supporting the syringe in an axial position relative to the outer housing, and
  an intermediate housing at least part of which is located within said outer housing and said syringe holder,
characterised in that said intermediate housing is provided with a blocking means capable of abutting the syringe or the syringe holder so as to be capable of preventing forward axial movement of the syringe when a forward axial force is applied to said needle before actuation of the autoinjector to deliver an injection, but incapable of preventing forward axial movement of the syringe during actuation of the autoinjector to deliver an injection.

Preferably the blocking means are capable of abutting the forwardmost part of the syringe or the syringe holder and/or said blocking means are moveable between a first blocking position in which said blocking means abut the syringe or syringe holder so as to block their axial path and a second, non-blocking position in which said blocking means do not block the axial path of the syringe or syringe holder.

In one embodiment, said blocking means are movable from said first position to said second position upon removal of a needle cover from said needle and/or removal of an end cap from the front end of the autoinjector. This automatic movement has the advantage of not requiring any positive additional action by the user, other than the normal removal of the autoinjector's end cap.

Preferably said blocking means comprise one or more radially-flexible fingers which are radially flexible substantially into and out of the axial path of said syringe or syringe holder.

In one embodiment, in said blocking position, the radially-flexible fingers are flexed inwardly by means of an interference fit with said outer housing and, in said non-blocking position, the radially-flexible fingers are flexed outwardly so as to locate in a recess or aperture in said outer housing.

In another embodiment, in said blocking position, the radially-flexible fingers are flexed inwardly by means of an interference fit with said end cap or said needle cover and, in said non-blocking position, the radially-flexible fingers are flexed outwardly so as to locate in a recess or aperture in said end cap or needle cover.

According to a second aspect of the invention, there is provided an autoinjector comprising an outer housing in which can be mounted a syringe for holding a volume of medicament, the syringe for holding medicament having a needle at one end thereof, a syringe holder for supporting the syringe in an axial position relative to the outer housing, and an inner housing at least part of which is intermediate said outer housing and said syringe holder, characterised in that one of said inner housing and syringe holder is provided with a gripping means for gripping the other of said inner housing and syringe holder so as to be capable of substantially preventing forward axial movement of the syringe when a forward axial force is applied to said needle, but incapable of preventing forward axial movement of the syringe during actuation of the autoinjector to deliver an injection.

Preferably, the autoinjector is a single-use autoinjector. The simple construction of the autoinjector makes it very appropriate for applications such as emergency use for injecting a large population to control a pandemic, where a large number of cost-effective disposable autoinjectors are required. A single-use autoinjector also provides a very convenient means for patients to administer their own injections, even if lacking in dexterity and/or experience.

Typically, the autoinjector contains an energy source, for example a spring, for moving said plunger axially in the barrel to deliver an injection in less than 30 seconds.

Preferably, the syringe is axially moveable in said housing and is biased so that the needle is normally wholly inside said housing, wherein before injection the syringe is movable axially so as to move at least a part of said needle out of the housing and wherein after injection, the syringe is able to retract in order to retract said part of said needle into the housing. The concealment of the needle both before and after injection makes the autoinjector particularly suitable where the patient has any aversion to injection by needle. Concealment of the needle both before and after injection also eliminates the risk of needle-stick injury.

Further features of the invention are defined in the appended claims.

BRIEF DESCRIPTION OF THE DRAWINGS

Preferred embodiments of the present invention will now be more particularly described, by way of example only, with reference to the accompanying drawings in which.

DETAILED DESCRIPTION

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

Features, integers, characteristics or groups described in conjunction with a particular aspect, embodiment or example of the invention are to be understood to be applicable to any other aspect, embodiment or example described herein unless incompatible therewith.

Figure 1:
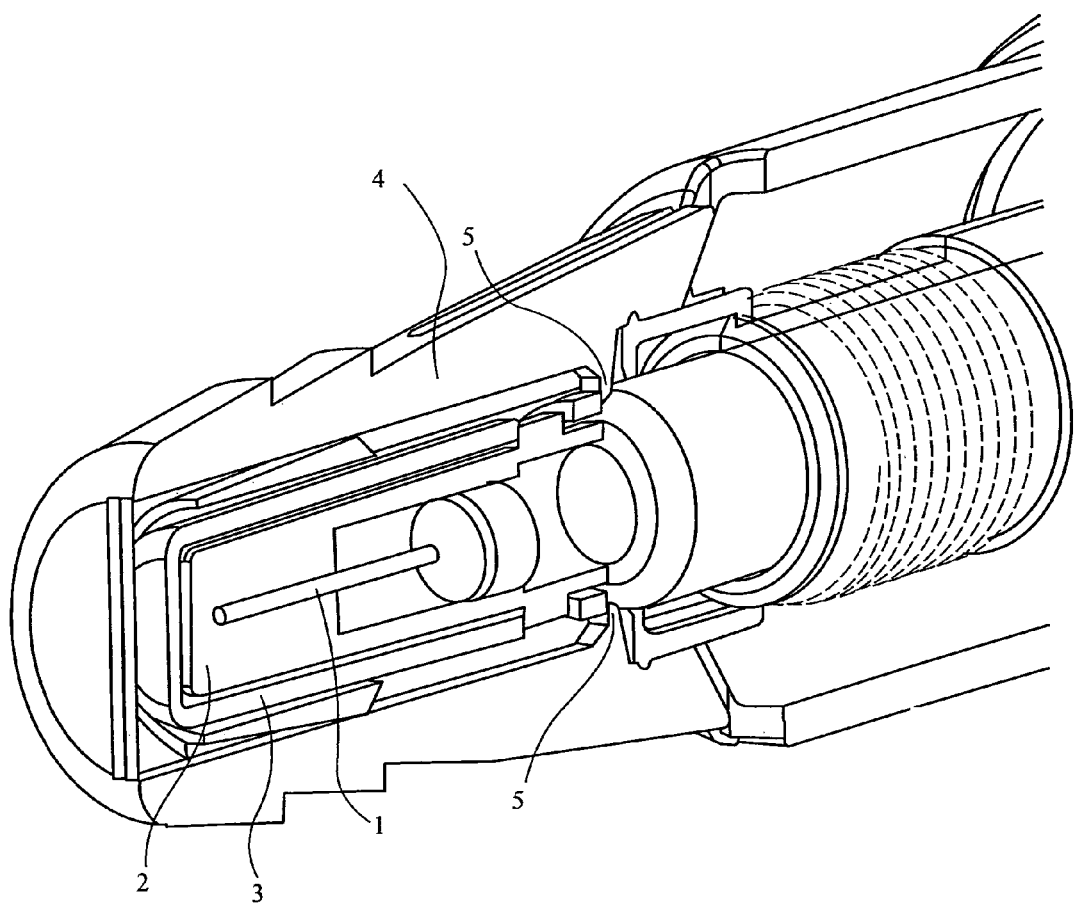
FIG. 1 (PRIOR ART) is a perspective view, partly in cross-section of the front end of a known autoinjector.

Referring to FIG. 1 (PRIOR ART), the autoinjector has an outer housing in which is contained a syringe comprising a barrel containing medicament and a needle 1 at the front end thereof. The needle 1 is embedded in a rubber moulding 2 which, in turn, is closely surrounded by a rigid, preferably nylon, needle cover 3. An endcap 4 protects all of these components and is attached to the front end of the autoinjector's outer housing.

The endcap, needle cover and rubber moulding are used to protect the needle end of the autoinjector during transit, storage and before use to deliver an injection. The endcap 4 has the further advantage of preventing accidental or unintended activation of the autoinjector, as it is not possible to fire the autoinjector with the endcap 4 in place.

The needle cover and rubber moulding are firmly fixed on the needle 1 and it is difficult, if not impossible, for a patient to pull them from the needle using his/her fingers alone because of their position inside the nozzle of the autoinjector. The outer endcap 4 is provided not only to improve the aesthetic appearance of the injection device, before use, but also serves the function of facilitating the removal of the nylon sheath and rubber moulding.

The endcap 4 is releasably retained on the front end of the injection device. When it is desired to remove the endcap 4 from the device, the patient grips the endcap and pulls axially in the direction indicated by the arrow. In the illustrated example, tabs 5 are urged against the rear of the needle cover 3 and sufficient force can be applied thereby to disengage the needle 1 from the rubber moulding 2. In this way, the entire moulding 2, needle cover 3 and endcap 4 can be removed from the autoinjector and discarded, so that the autoinjector is then ready to use. Other variants of the same principle are also known.

As mentioned above, a problem is that as the rubber moulding is pulled from the needle, the needle is subjected to an axial force which in turn pulls the syringe (to which the needle is attached) axially forward. When the needle comes free of the rubber sheath, the forward axial force is suddenly removed and the barrel of the syringe can "bounce back" against other internal components of the autoinjector.

The barrel of a syringe is usually glass, since glass has the most favourable storage properties for many drugs. However, glass is notoriously fragile and there is a risk of damage or breakage of the syringe if the forces to which the syringe is subjected are not properly controlled. The applicant has recognised that there is a risk of breakage caused by the "bounce back" described above. Syringe barrels made of materials other than glass, for example polyethylene or cyclic olefin polymers are less brittle when subjected to normal forces during injection, but still would benefit from the invention described herein.

The risk of the syringe breaking is not only inconvenient and costly but is also potentially dangerous. If breakage occurs, it is possible that glass fragments and/or the needle may become detached and exit the front of the device causing injury. Furthermore, there is the risk that the remaining medicament will leak or be ejected from the device in an uncontrolled manner, potentially delivering the wrong dose into the patient, or causing injury e.g. if the medicament contacts the patient's skin or eyes.

Figure 2:
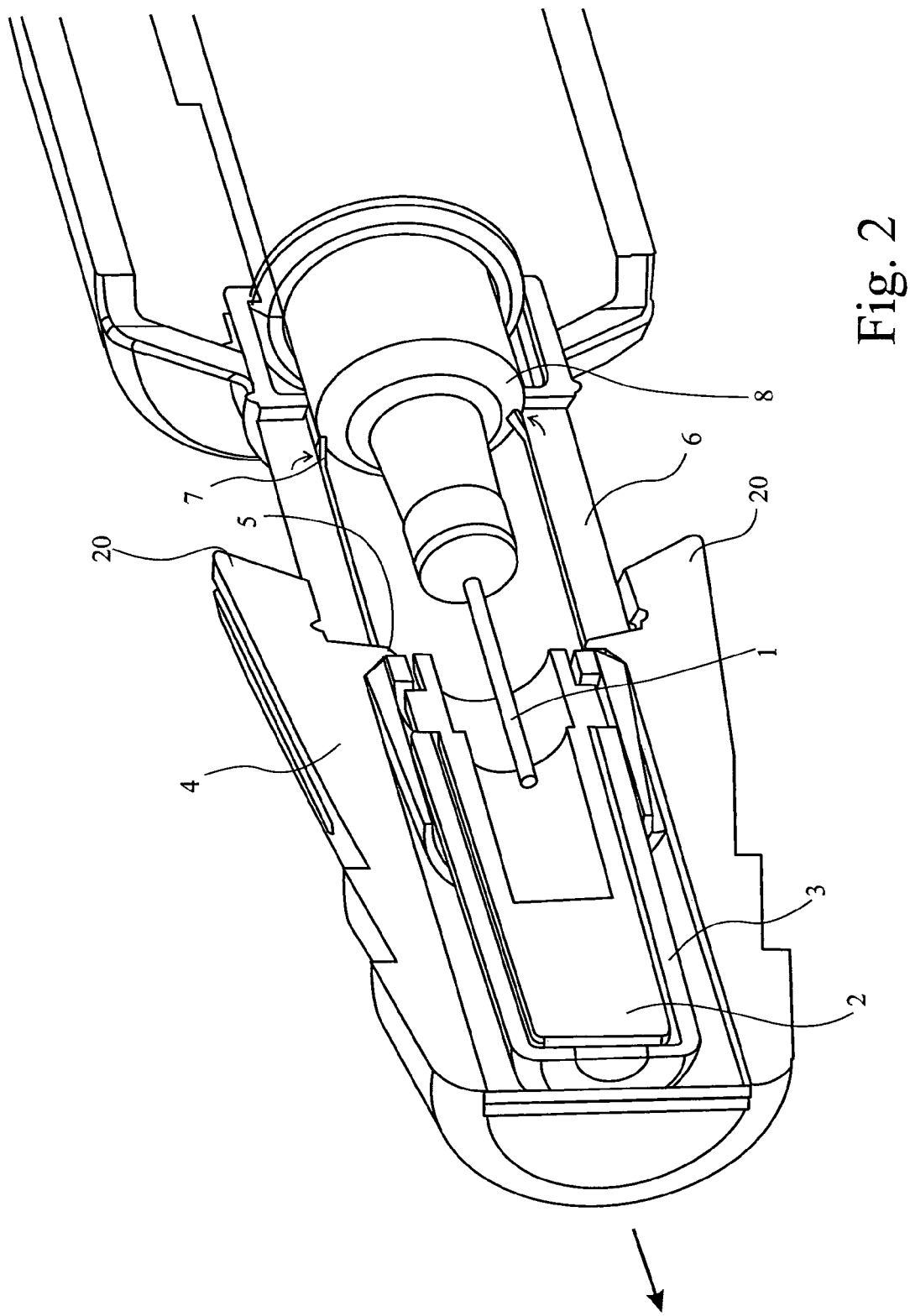
FIG. 2 is a side view, partly in cross-section of the front end of an autoinjector according to a first embodiment of the invention.

One embodiment of the invention is illustrated in FIG. 2. The front housing 6 of the autoinjector is provided with gripping means in the form of one or more flexible fingers 7. These fingers are initially forced radially-outwardly by the presence of the needle cover 3. However, as soon as a gap is created behind the needle cover 3 as it begins to be pulled axially from the needle 1, the fingers 7 flex radially-inwardly so as grip and to prevent the front of the barrel 8 and/or syringe support means moving axially forward too.

However, the flexible fingers 7 are relatively weak and are not resilient enough to resist the significantly stronger forward axial force supplied by the autoinjector's main energy source (usually a spring). When the autoinjector is actuated for delivery of an injection, the rapidly forward moving barrel 8 and/or syringe support means forces the fingers 7 radially-outwardly, out of their path. Tapering of the abutting surfaces of the fingers 7 and barrel may facilitate this.

Figure 3:
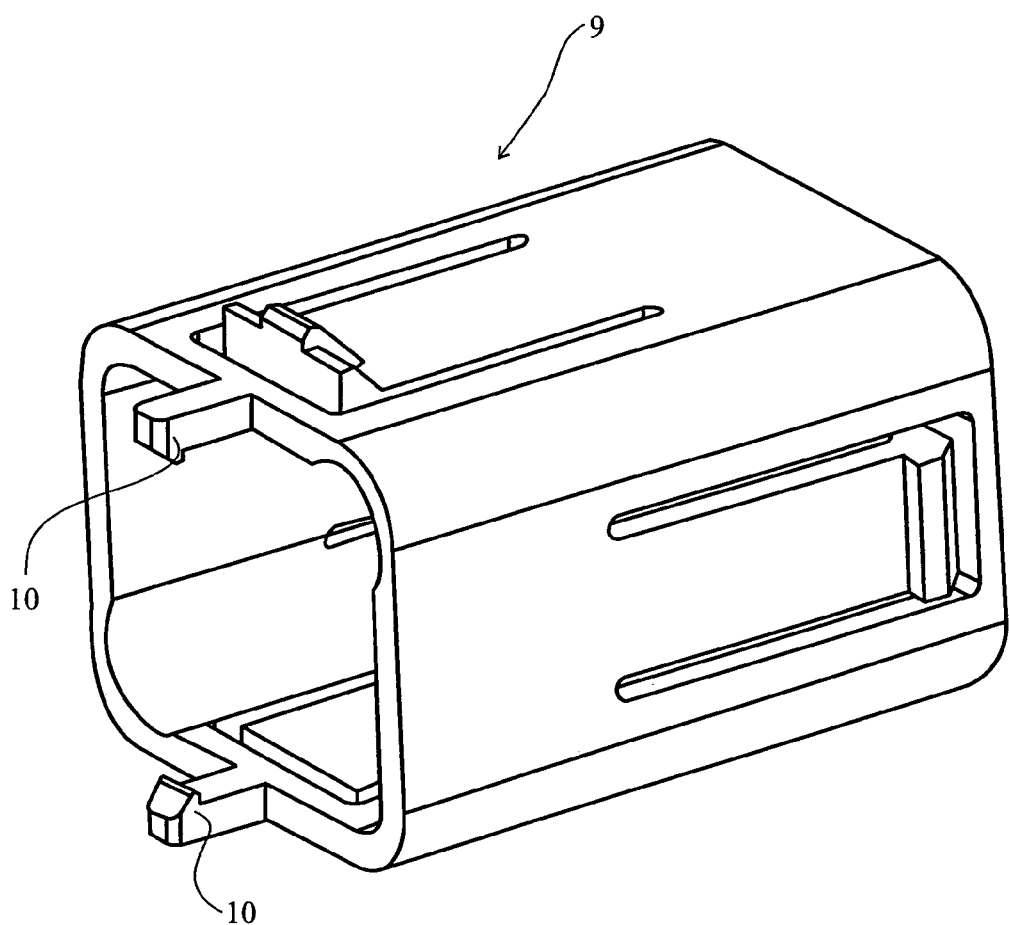
FIG. 3 is a perspective view of the modified inner housing of an autoinjector according to a second embodiment of the invention.
Figure 4:
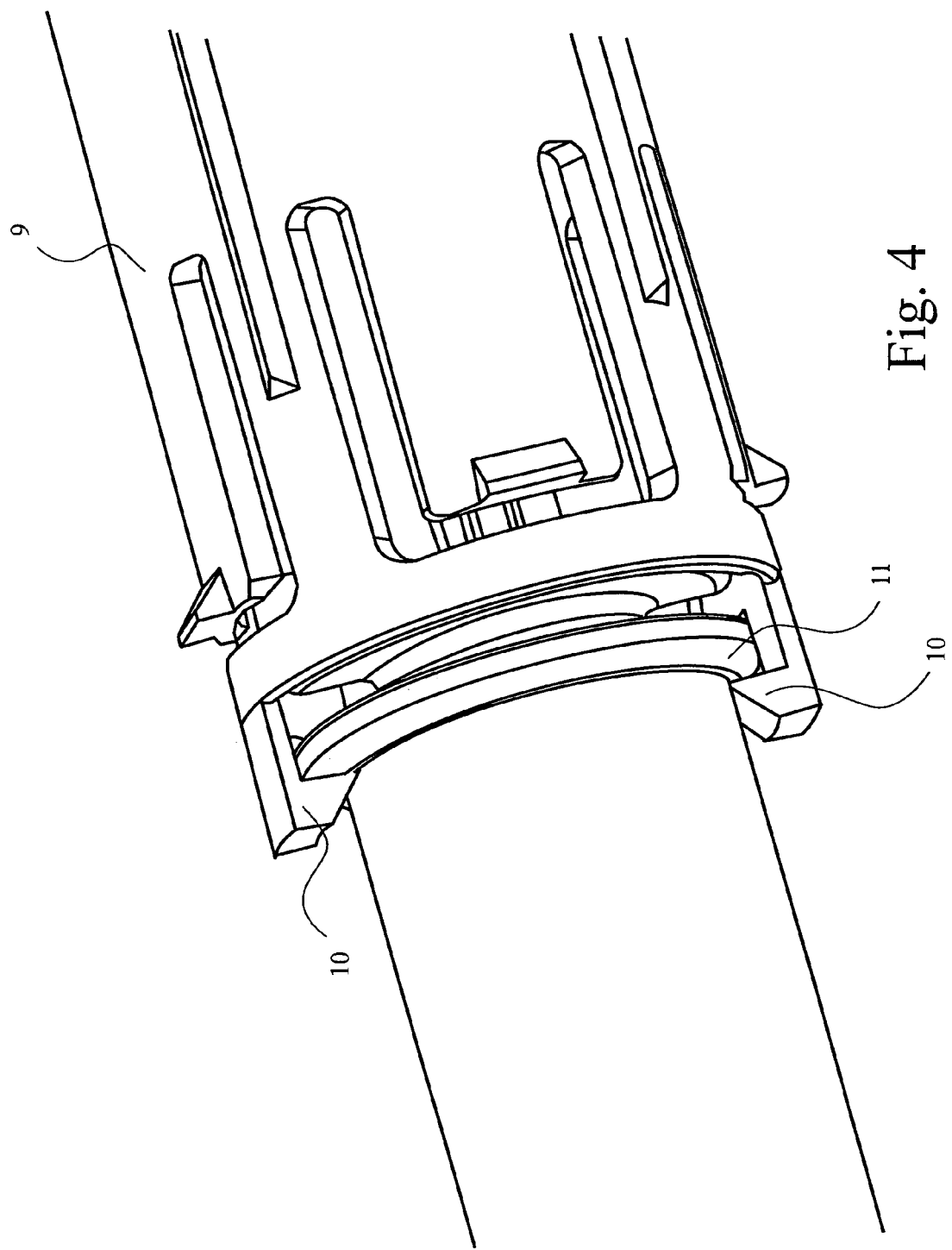
FIG. 4 shows how the inner housing of FIG. 3 grips a syringe holder to prevent axial movement of the syringe holder and syringe contained therein.

A second embodiment of the invention is illustrated in FIG. 3. FIG. 3 shows a modified inner housing 9 for an autoinjector of the type described in, for example, WO 2005/070481. The inner housing 9 is provided with gripping means in the form of one or more barbed hooks 10 at the front end thereof. FIG. 3 shows an inner housing 9 having a generally square cross-sectional shape, but as illustrated in FIG. 4 an inner housing of generally circular cross-sectional shape (as in WO 2005/070481) may equally be provided with hooks 10. As shown in FIG. 4, the hooks 10 are designed to grip the finger flange of a syringe barrel and/or to grip the flange seat 11 of a syringe holder of the type described in, for example, WO 2005/070481.

As with the flexible fingers of the first embodiment, the hooks 10 are strong enough to substantially prevent forward axial movement of the barrel and/or syringe holder caused by pulling the rubber moulding from the needle. However, the hooks 10 are not strong enough to resist the axial force supplied by the autoinjector's main energy source. When the autoinjector is actuated for delivery of an injection, the inner housing 9 moves rapidly forwards together with the syringe holder and therefore hooks 10 do not affect the actuation of the device to deliver an injection. In any case, the hooks 10 are relatively weak and capable of being forced radially-outwardly, out of the axial path of the syringe holder.

In the embodiments illustrated in FIGS. 3 and 4, the gripping means (hooks 10) are located on the inner housing and grip the flange seat of the syringe holder and/or finger flange of the barrel. Alternatively, the gripping means could be located on the flange seat of the syringe holder so as to grip a part of the inner housing.

Figure 5:
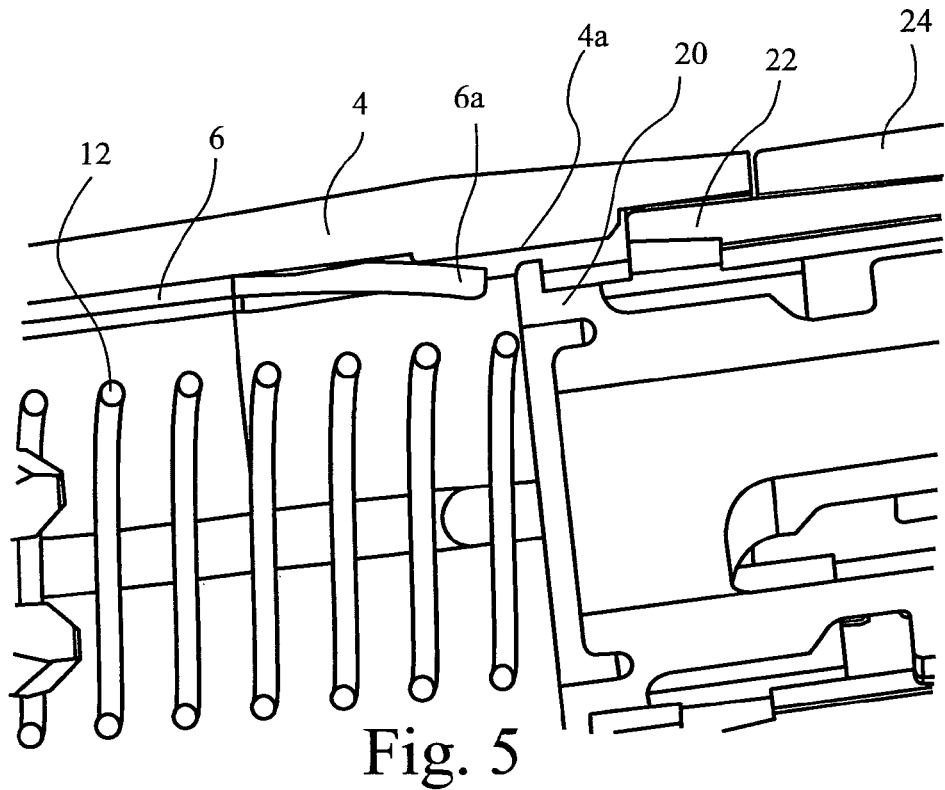
FIG. 5 is a partial cross sectional view of an autoinjector according to a third embodiment of the invention, wherein a flexible lever is urged radially inwards preventing axial movement of the syringe holder and syringe contained therein.
Figure 6:
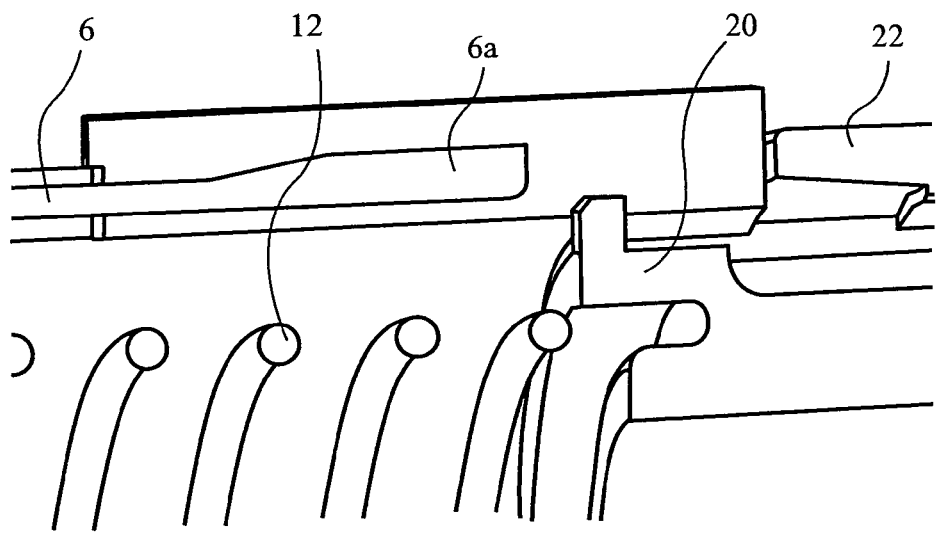
FIG. 6 is a partial cross sectional view of the autoinjector of FIG. 5, wherein the endcap has been removed and the flexible lever is in a relaxed state.

A further embodiment is illustrated in FIGS. 5 and 6. FIG. 5 shows an intermediate housing which, in this case, is the front housing 6 of the device. At least part of the front housing 6 is located within an outer housing 24 and preferably intermediate the outer housing 24 and syringe holder 20. At least one radially-flexible lever 6a is attached to or is part of the front housing providing blocking means which will be described in more detail below, In the specific embodiment of FIG. 5, the intermediate housing comprises the front housing 6, although it should be noted that the blocking means (e.g. lever 6a) described in connection with FIGS. 5 and 6 may alternatively be attached to a rear housing of the device. The lever 6a is radially-flexible such that when the endcap 4 is in place on the front end of the outer housing 24, the lever 6a is urged radially inwards into the axial path of the syringe holder 20 by interference with a rib 4a projecting radially inwards from the endcap 4. Thus, when the endcap 4 is in place, the front end of syringe holder 20 abuts the lever 6a, preventing forward axial movement of the syringe holder 6a and syringe contained therein. It is preferred that the lever 6a normally abuts the front end of the syringe holder 20, although it is envisaged that a small gap may be present. However, such a gap is less desirable and should be minimised.

When the patient is ready to use the autoinjector, he pulls the endcap 4 off the device axially forwards. Simultaneously, the needle cover (not illustrated) is pulled from the needle. Once the needle cover is clear of the needle (and the point at which "bounceback" might occur when forward axial force on the needle is suddenly released has passed), the rib 4a passes over the lever 6a and eventually clears it such that the lever 6a is no longer urged radially inwards and is free to spring radially out of the axial path of the syringe holder 20 as shown in FIG. 6. The communicating surfaces of the rib 4a and the lever 6a may be tapered to facilitate smooth movement therebetween.

FIG. 6 shows the lever 6a in a relaxed position following the removal of the endcap 4. Once the endcap 4 is completely removed, the syringe holder 20 is free to move axially forward when the device is actuated to deliver an injection.

Figure 7:
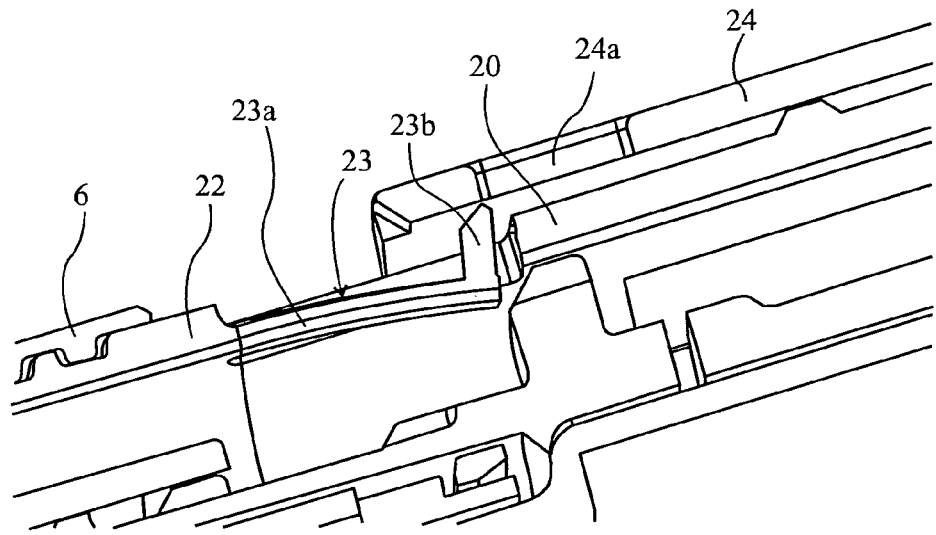
FIG. 7 is a partial cross sectional view of an autoinjector according to a fourth embodiment of the invention, wherein a flexible lever is urged radially inwards preventing axial movement of the syringe holder and syringe contained therein.
Figure 8:
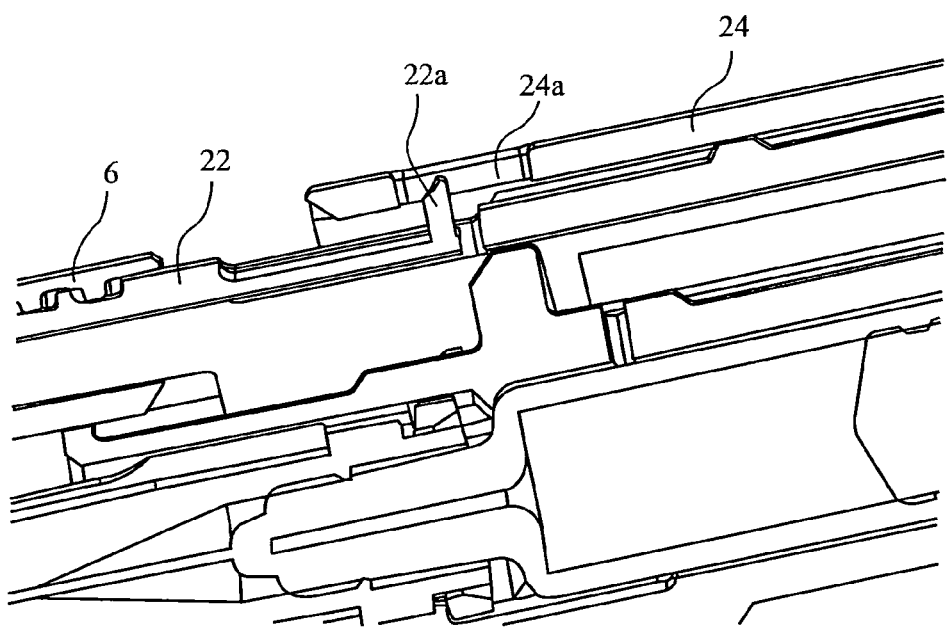
FIG. 8 is a partial cross sectional view of the autoinjector of FIG. 7, wherein the lever is in relaxed state following the forward movement of the outer housing.

A further embodiment is illustrated in FIGS. 7 and 8. FIG. 7 discloses an alternative mechanism for preventing undesired forward axial movement of the syringe holder 20. In the specific embodiment of FIG. 7, blocking means are provided in the form of at least one lever 23 attached to the rear housing 22, wherein the rear housing 22 is an intermediate housing according to the definition above. The lever 23 comprises two sections; a radially flexible first section 23a extending from the rear housing 22 substantially parallel the longitudinal axis of the device, and a preferably non-resilient second section 23b projecting radially outwards, substantially perpendicular to the first section 23a.

Prior to actuating the device to deliver an injection, as shown in FIG. 7, the second section 23b abuts an inner surface of the outer housing 24 urging the lever 23 radially inwards into the axial path of the syringe holder 20. When flexed inwards, the presence of the lever 23 prevents forward axial movement of the syringe holder 20 and syringe. Therefore, when the endcap and needle sheath are removed from the front of the device, "bounceback" of the syringe holder and/or syringe is prevented.

Upon actuating the device to deliver an injection, forward movement of the outer housing 24 relative to the rear housing 22 causes the second section 23b to move into an aperture 24a in the outer housing 24 when the two become aligned transverse the longitudinal axis. Alternatively, the outer housing 24 may have a recess into which the second section 23b can move into. The communicating surfaces of the lever 23 and outer housing 24 may be tapered to facilitate easy movement of the lever 23 into the aperture 24a. Movement of the second section 23b into the aperture 24a causes the lever 23 to flex radially outwards, out of the axial path of the syringe holder 20. FIG. 8 shows the lever 23 in a relaxed state, with the second section 23b aligned with the aperture 24a transverse the longitudinal axis of the device. In the relaxed state, the syringe holder 20 and syringe are free to move axially forward upon actuation of the device.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. An autoinjector comprising an outer housing in which can be mounted a syringe for holding a volume of medicament, the syringe for holding medicament having a needle at one end thereof, a syringe holder for supporting the syringe in an axial position relative to the outer housing, and an intermediate housing at least part of which is located within said outer housing, the syringe being moveable along an axial path relative to the outer housing upon actuation of the autoinjector to deliver an injection, said intermediate housing being provided with a blocking means capable of abutting the syringe or the syringe holder so as to be capable of preventing forward axial movement of the syringe when a forward axial force is applied to said needle before actuation of the autoinjector to deliver an injection, but incapable of preventing forward axial movement of the syringe during actuation of the autoinjector to deliver an injections;

wherein said blocking means are moveable between a first blocking position in which said blocking means abut the syringe or syringe holder so as to block their axial path and a second, non-blocking position in which said blocking means do not block the axial path of the syringe or syringe holder;

said blocking means comprising one or more fingers that are radially flexible substantially into and out of the axial path of said syringe or syringe holder; and wherein in the first blocking position the one or more radially flexible fingers are urged into the axial path of the syrinyringe holder, and, when no longerurged radially inwards, the one or more radially flexible fingers spring out of the axial path of the syringe or syringe holder to the second non-blocking position.

2. The autoinjector as claimed in claim 1 wherein said blocking means are capable of abutting the forwardmost part of the syringe or the syringe holder.

3. The autoinjector of claim 2 wherein said blocking means are movable from said first position to said second position upon removal of a needle cover from said needle and/or removal of an end cap from the front end of the autoinjector.

4. The autoinjector as claimed in claim 1 wherein said blocking means are movable from said first position to said second position upon removal of a needle cover from said needle and/or removal of an end cap from the front end of the autoinjector.

5. The autoinjector of claim 1 wherein, in said blocking position, the radially-flexible fingers are flexed inwardly by means of an interference fit with said outer housing.

6. The autoinjector of claim 5 wherein, in said non-blocking position, the radially- flexible fingers are flexed outwardly so as to locate in a recess or aperture in said outer housing.

7. The autoinjector of claim 1 wherein, in said blocking position, the radially-flexible fingers are flexed inwardly by means of an interference fit with said end cap or said needle cover.

8. The autoinjector of claim 7 wherein, in said non-blocking position, the radially- flexible fingers are flexed outwardly so as to locate in a recess or aperture in said end cap or needle cover.

9. The autoinjector of claim 1 wherein said intermediate housing is a front housing of the autoinjector.

10. The autoinjector of claim 1 wherein said intermediate housing is a rear housing of the autoinjector.

11. The autoinjector as claimed in claim 1 wherein said forward axial force is a pulling force on said needle.

12. The autoinjector of claim 1 wherein said autoinjector is a single-use autoinjector.

13. The autoinjector of claim 1 further comprising an energy source capable of delivering an injection from the syringe in less than 30 seconds.

14. The autoinjector of claim 13 further comprising an inner housing moveable by said energy source between three positions, namely a first position in which the inner housing is in communication with the barrel of the syringe such that, in use, the barrel is movable axially so as to move at least part of said needle out of the outer housing; a second position in which the inner housing is in communication with a plunger of the syringe but not the barrel such that, in use, said plunger is movable axially into said barrel so as to expel medicament through the needle; and a third position in which the inner housing is in communication with neither the plunger nor the barrel such that, in use, the plunger and barrel are able to retract in order to retract the needle into the outer housing.

15. The autoinjector of claim 14 wherein said inner housing is a unitary component.

16. The autoinjector of claim 1 wherein the syringe is axially moveable in said housing and is biased so that the needle is normally wholly inside said housing, wherein before injection the syringe is movable axially so as to move at least a part of said needle out of the housing and wherein after injection, the syringe is able to retract in order to retract said part of said needle into the housing.

17. The autoinjector of claim 1 wherein said syringe holder is generally cylindrical and of a diameter less than the diameter of the finger flange of the syringe so that the syringe support means is suitably sized to closely surround the barrel of the syringe, in use.

18. The autoinjector as claimed in claim 1, in which is mounted a syringe for holding a volume of medicament, the syringe having a needle at one end thereof.

\* \* \* \* \*